(12) United States Patent
Wada et al.

(10) Patent No.: US 7,755,497 B2
(45) Date of Patent: Jul. 13, 2010

(54) URINE SENSOR

(75) Inventors: Ichiro Wada, Kagawa-ken (JP); Miou Suzuki, Kagawa-ken (JP); Kiyoshi Toda, Tokyo (JP); Yuichi Hirai, Tokyo (JP); Masaho Hayashi, Tokyo (JP); Hiroshi Uematsu, Tokyo (JP); Toshihiko Uenishi, Fukuoka (JP)

(73) Assignee: Uni-Charm Corporation (JP)

( * ) Notice: Subject to any disclaimer, the term of this patent is extended or adjusted under 35 U.S.C. 154(b) by 876 days.

(21) Appl. No.: 11/457,005

(22) Filed: Jul. 12, 2006

(65) Prior Publication Data

US 2007/0035405 A1 Feb. 15, 2007

(30) Foreign Application Priority Data

Jul. 13, 2005 (JP) ............................. 2005-204978
Jul. 6, 2006 (JP) ............................. 2006-187166

(51) Int. Cl.
*G08B 21/00* (2006.01)
(52) U.S. Cl. ...................................... 340/604; 340/605
(58) Field of Classification Search .................. 340/604
See application file for complete search history.

(56) References Cited

U.S. PATENT DOCUMENTS

| 4,264,901 | A | * | 4/1981 | Petersen et al. ............. 340/604 |
| 4,356,818 | A | * | 11/1982 | Macias et al. ................ 128/886 |
| 4,677,371 | A | * | 6/1987 | Imaizumi ..................... 324/544 |
| 4,688,027 | A | * | 8/1987 | Widener ...................... 340/604 |
| 4,747,166 | A | | 5/1988 | Kuntz |
| 5,681,297 | A | | 10/1997 | Hashimoto et al. |
| 5,790,036 | A | * | 8/1998 | Fisher et al. ................. 340/605 |
| 2005/0070861 | A1 | * | 3/2005 | Okabe et al. ................ 604/327 |

FOREIGN PATENT DOCUMENTS

| EP | 1457178 | | 9/2004 |
| JP | 63-290950 | * | 11/1988 |
| JP | 02-174846 | * | 7/1990 |
| JP | 02174846 | | 7/1990 |
| JP | 614741 | | 4/1994 |
| JP | 07239990 | | 9/1995 |
| JP | 09033468 | | 2/1997 |
| JP | 11-295250 | * | 10/1999 |
| JP | 11295250 | | 10/1999 |
| JP | 2002243677 | | 8/2002 |
| JP | 2004-267517 | | 9/2004 |

* cited by examiner

*Primary Examiner*—Daniel Wu
*Assistant Examiner*—Brian Wilson
(74) *Attorney, Agent, or Firm*—Lowe Hauptman Ham & Berner, LLP

(57) ABSTRACT

Here is disclosed a urine receiver. The urine receiver comprises a container member adapted to suck urine discharged from a wearer of the urine receiver and a urine sensor provided with a pair of electrodes interposed between the container member and the wearer's skin and serving to detect the urine. The paired electrodes covered with insulating coating. The coating is formed with through-holes adapted to expose a limited area of the electrodes.

20 Claims, 11 Drawing Sheets

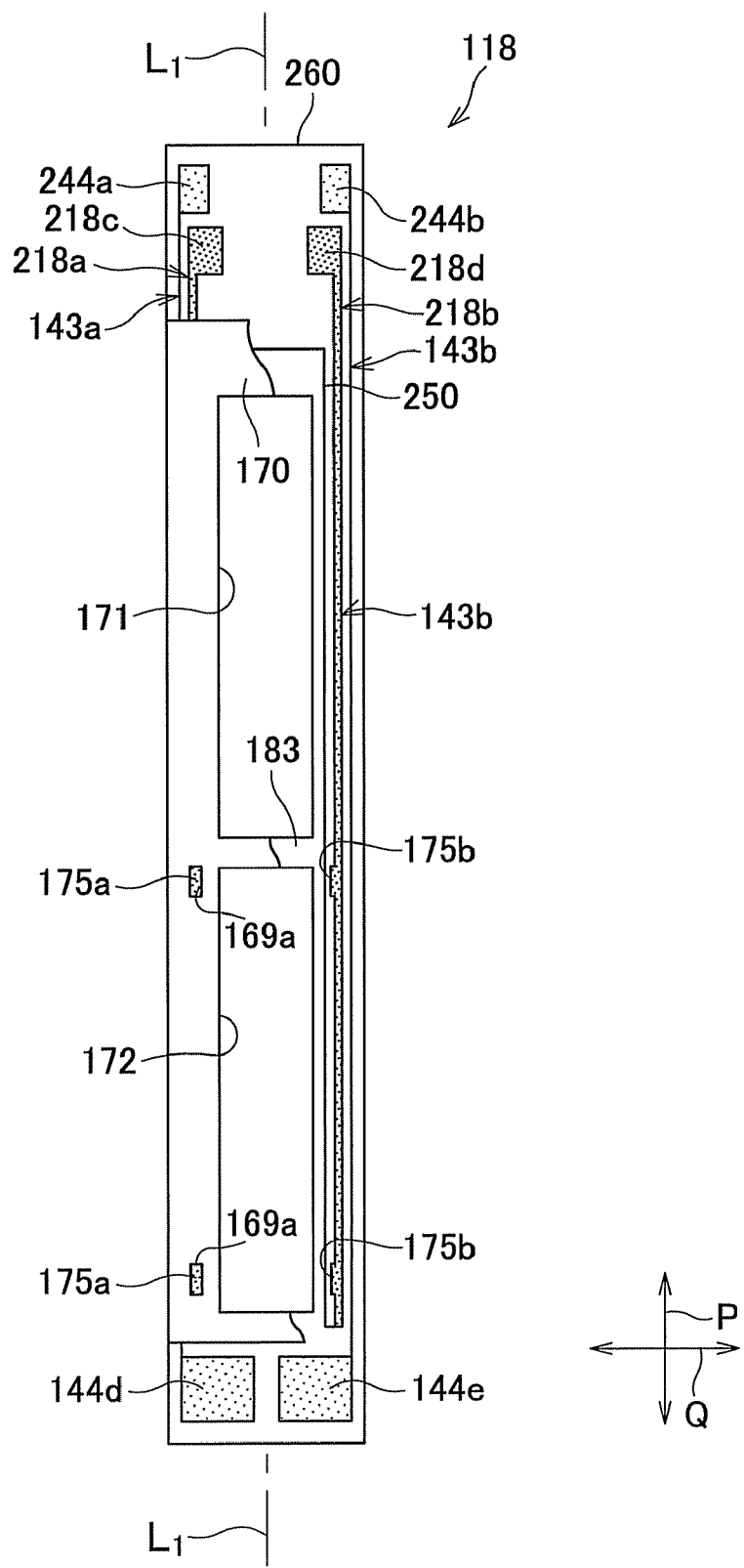

URINE SENSOR

BACKGROUND OF THE INVENTION

The present invention relates to generally a urine sensor to be used with an automatic urine disposal system for persons such as bedridden aged, bedridden patient and physically disabled persons for whom it is difficult to control timing of urination and/or to make a disposal of urine after discharged.

It is often difficult for those persons as have been described above to control timing of urination on his or her own will and/or to make disposal of urine after discharged by his or her own ability. In order to overcome the difficulties for such persons, there has already been proposed an automatic urine disposal system comprising a urine receiver to be put against a wearer's crotch around a urethral, suction means such as a suction pump provided separately of the urine receiver adapted to guide the amount of urine collected by the suction means in the urine receiver to a urine reservoir. The suction pump evacuates air within the hermetically sealed urine reservoir to generate a differential pressure between the urine receiver and the urine reservoir so that the differential pressure causes the amount of urine within the urine receiver to be guided into the urine reservoir.

This urine receiver of prior art includes a urine sensor to detect urination and thereupon to activate the suction pump. The urine sensor includes a pair of electrodes and a urination detection circuit adapted to become live and to activate the suction pump when the paired electrodes are electrically connected to each other via urine. The urine receiver of this type, for example, disclosed by Japanese Laid-Open Patent Application No. 2004-267517A comprises a topsheet, a urine absorbent sheet, a urine backflow prevention sheet and a pair of electrodes constituting the urine sensor interposed between the topsheet and the urine backflow prevention sheet. In the case of this urine sensor, the urine backflow prevention sheet functions to prevent backflow of urine from the urine absorbent sheet toward the urine sensor and, even if urine is quickly absorbed by the urine absorbent sheet and still stays thereon, no erroneous signal indicating urination is output on the basis of such urine staying on the urine absorbent sheet.

However, the electrodes used in this urine sensor of prior art have a relatively large area entirely exposed and consequentially the suction pump may erroneously be activated due to a contact between the electrodes and the topsheet on which an amount of urine stays. In addition, depending on a posture of a wearer of the urine receiver, the topsheet may come in contact with the urine sensor and erroneously activate the suction pump.

SUMMARY OF THE INVENTION

In view of the problems described above, it is an object of the present invention to prevent the urine sensor included in the urine receiver from erroneously activating a suction pump.

According to the present invention, there is provided a urine sensor to be used in a urine receiver comprising a urine collecting member to be put on a wearer's body with the inner side placed against a urethral and a skin thereabout and a urine detecting member to be interposed between the wearer's skin and the urine collecting member and serving to detect urine discharged from the urethral, wherein the urine receiver is connected to vacuum suction means provided separately of the urine receiver so that the vacuum suction means may be activated in response to a detection signal output from the urine detecting member to suck the urine into the urine collecting member.

The urine sensor comprises thermoplastic synthetic resin film having a length direction, a width direction and a thickness direction being orthogonal one to another, a pair of electrodes formed on a surface of the film and an electrically insulating coating formed on the surface to cover the electrodes, the film being formed along a center line bisecting the width of the film with an opening and both side portions of the film along the opening being respectively provided with the electrodes extending in the length direction, each of the electrodes being provided at one end of the opposite ends thereof as viewed in the length direction with an electrical connector means to be connected to the vacuum suction means, the insulating coating being formed between the opposite ends of the electrodes with a plurality of through-holes in which the electrodes may come in contact with the urine flowing into the through-holes.

According to one embodiment, respective ends of the pair of electrodes opposed to the one ends are electrically connected to each other via a circuit having an electric resistance higher than those of the electrodes.

According to another embodiment, each of the electrodes has an electric resistance of 150 KΩ or less and the circuit has an electric resistance of in a range of 2 to 10 MΩ.

According to still another embodiment, the urine sensor includes a pair of feces detection electrodes provided separately of a pair of the electrodes so as to extend in parallel to these electrodes and the feces detection electrodes are also covered with the electrically insulating coating including coating-free zones in the vicinity of the ends opposed to the respective one ends so that the coating-free zones are allowed to contact feces to be detected.

According to further another embodiment, the electrodes, the circuit and the feces detection electrodes are formed by conductive ink or conductive coating material.

According to an embodiment of the present invention, the electrodes for the urine sensor are formed on the surface of the thermoplastic synthetic resin film so as to extend on both sides of the opening formed in this film and covered with the insulator coating. The insulator coating is formed with a plurality of through-holes in which the electrodes are partially exposed and, when these exposed portions of the electrodes are wet with urine, the pair of electrodes are electrically connected to each other. In this way, urination can be reliably detected without erroneously activating the vacuum suction means.

According to an embodiment of the present invention wherein the respective ends of the pair of electrodes are electrically connected to each other via the circuit having an electrical resistance higher than those of these electrodes, this circuit can be used as a means to detect whether a wiring breakage occurs or not in these paired electrodes.

According to an embodiment of the present invention wherein feces can be detected, the urine receiver can be replaced in a timely manner before it loses a capability of urine collection.

BRIEF DESCRIPTION OF THE DRAWINGS

FIG. 11 is a view similar to FIG. 6, showing one embodiment of the urine sensor.

DETAILED DESCRIPTION OF THE PREFERRED EMBODIMENTS

Details of the urine sensor according to the present invention will be more fully understood from the description given hereunder in reference with the accompanying drawings.

Figure 1:
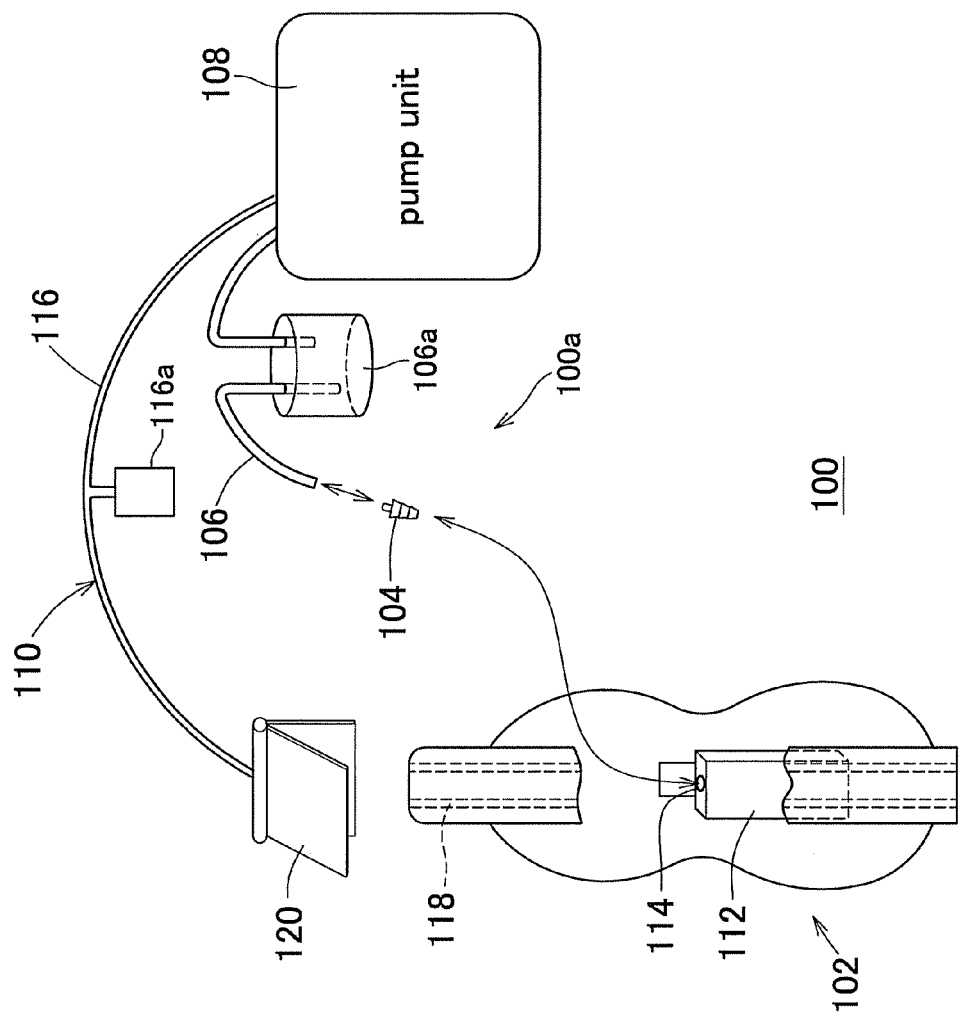
FIG. 1 is a schematic diagram illustrating a construction of an automatic urine disposal system including a urine receiver.

FIG. 1 is a diagram schematically illustrating a construction of an automatic urine disposal system 100 including a urine suction mechanism 100a to be combined with a urine receiver 102 according to the invention. While the urine receiver 102 has an inner side member facing the wearer's skin and an outer side member facing the wearer's clothes, the outer side member is shown as partially broken away.

The automatic urine disposal system 100 is adapted to collect urine discharged from the wearer (not shown) by the urine receiver 102 for disposal. The urine receiver 102 includes a tray-like container member 112 to face the wearer's skin in the vicinity of the urethral and to receive urine discharged while the automatic urine disposal system 100 includes the urine suction mechanism 100a comprising various components such as a joint member 104, a urine guide tube 106 and a pump unit 108.

The pump unit 108 comprises a urine reservoir 106a adapted to take over the amount of urine having been collected by the urine receiver 102 and to pool this, electric wiring 116 serving for an electrical connection of a urine sensor 118 provided on the urine receiver 102 for detection of urination to the pump unit 108, and a suction pump (not shown) adapted to be activated in response to a signal transmitted from the urine sensor 118 via the wiring 116. In the urine receiver 102, a peripheral wall of the container member 112 is formed with a urine evacuation opening 114 and the urine guide tube 106 is connected to this opening 114 by means of the joint member 104. The wiring 116 extending from the pump unit 108 is provided at its distal end with a clip 120 serving for electric connections of electrodes 218a, 218b (see FIG. 3) of the urine sensor 118 and others provided in the urine receiver 102 to the wiring 116. Such an automatic urine disposal system 100 detects a urination by the urine sensor 118 and the suction pump included in the pump unit 108 is activated in response to the detection signal. The pump unit 108 vacuums up air within the urine reservoir 106a so that the urine discharged from the wearer may be forcibly guided into the container member 112 and eventually collected into the urine reservoir 106a via the joint member 104 and the urine guide tube 106.

Figure 2:
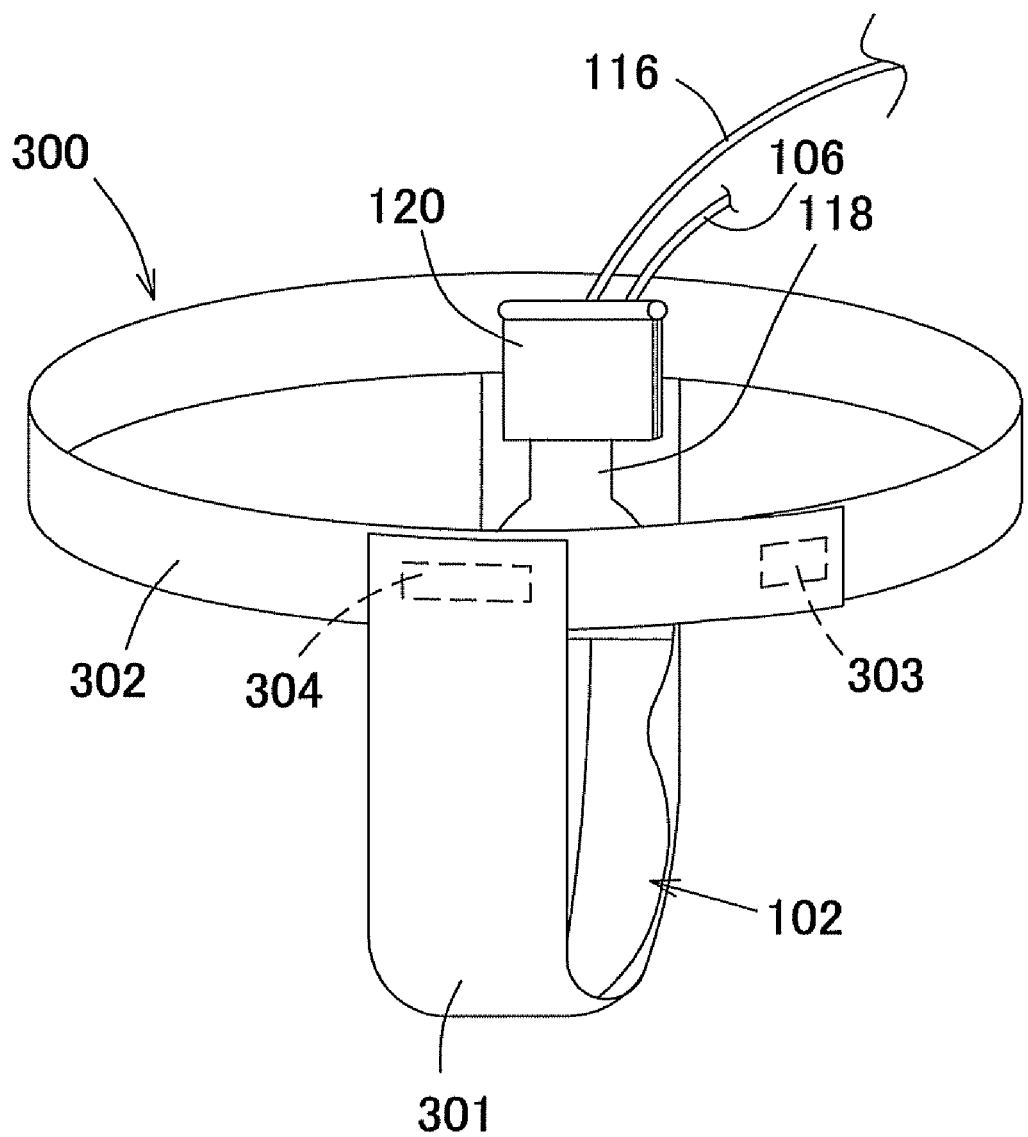
FIG. 2 is a diagram showing the urine receiver as put on a wearer.

FIG. 2 is a diagram exemplarily illustrating how to wear the urine receiver 102. The urine receiver 102 is fixed to the inner side of a crotch belt section 301 constituting a T-shaped belt 300 by means of, for example, a pressure-sensitive adhesive or a mechanical fastener known in a trade name of Magic Tape. Being put on the wearer's body, a major part of the container member 112 of the urine receiver 102 extends in the vertical direction of the wearer's body with the inner side facing the urethral and the skin extending therearound while a lower end of the container member 112 extends toward the anus so as to describe a gentle curve. In the T-shaped belt 300, longitudinally opposite ends of a waist belt section 302 are detachably connected to each other by a suitable connector means 303 such as a mechanical fastener while the crotch belt section 301 has end stitched together with the waist belt section 302 and the other end detachably connected to the waist belt section 302 by means of the mechanical fastener 304. It should be noted here that the chassis for the urine receiver 102 is not limited to the illustrated T-shaped belt and the other appropriate means such as the open- or pants-type diaper, the diaper cover or the pants for incontinent patient can be used as the chassis for the urine receiver 102.

Figure 3:
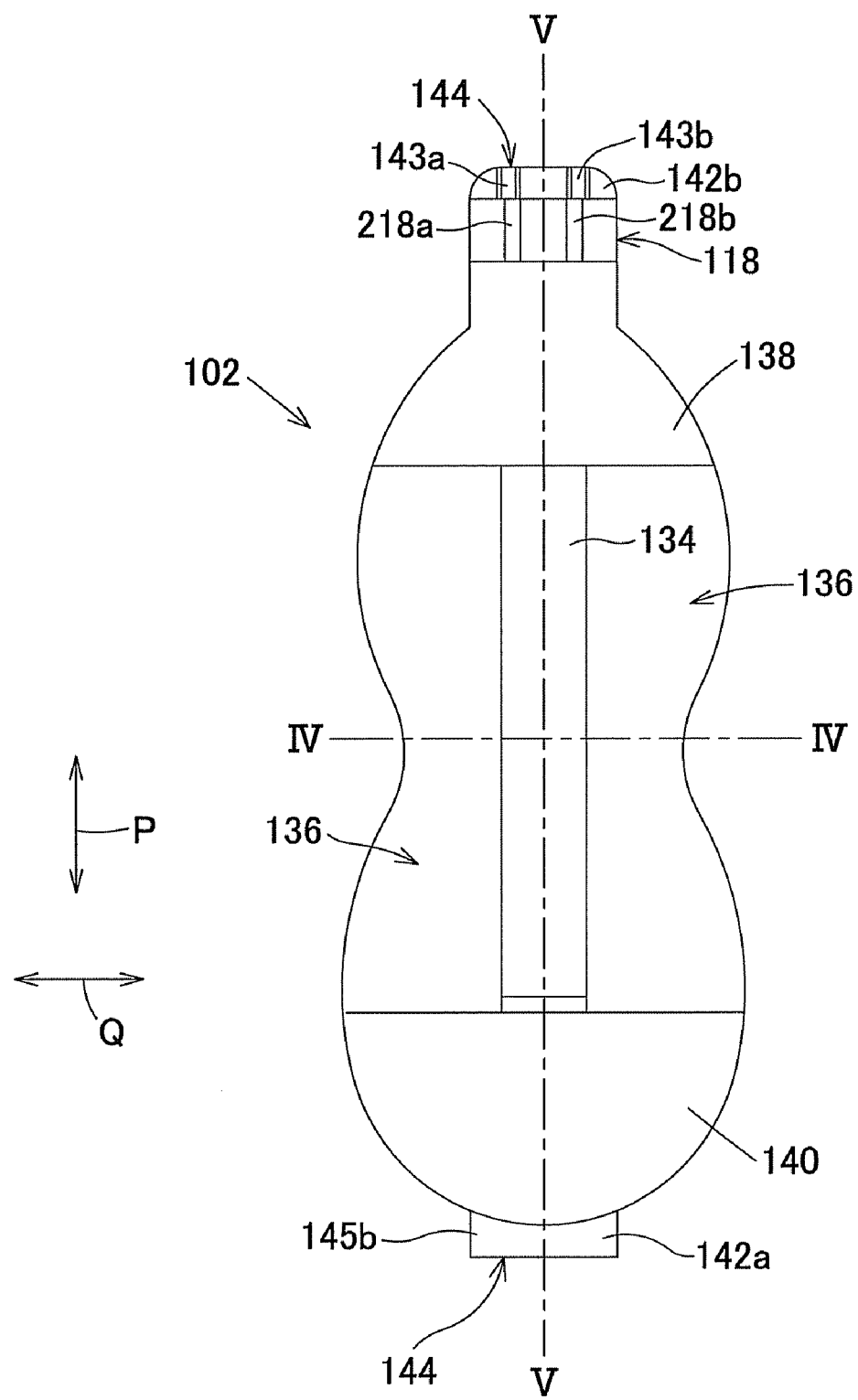
FIG. 3 is a plan view of the urine receiver.
Figure 4:
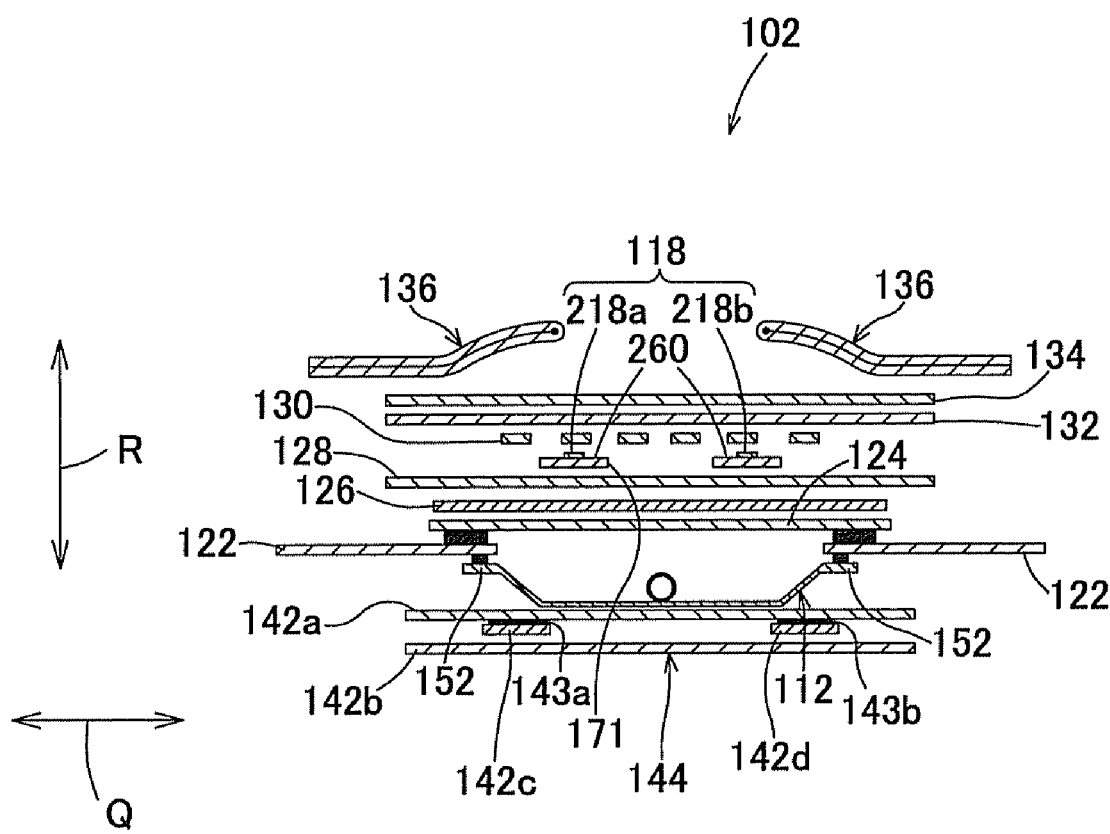
FIG. 4 is a sectional view taken along the line IV-IV in FIG. 3.
Figure 5:
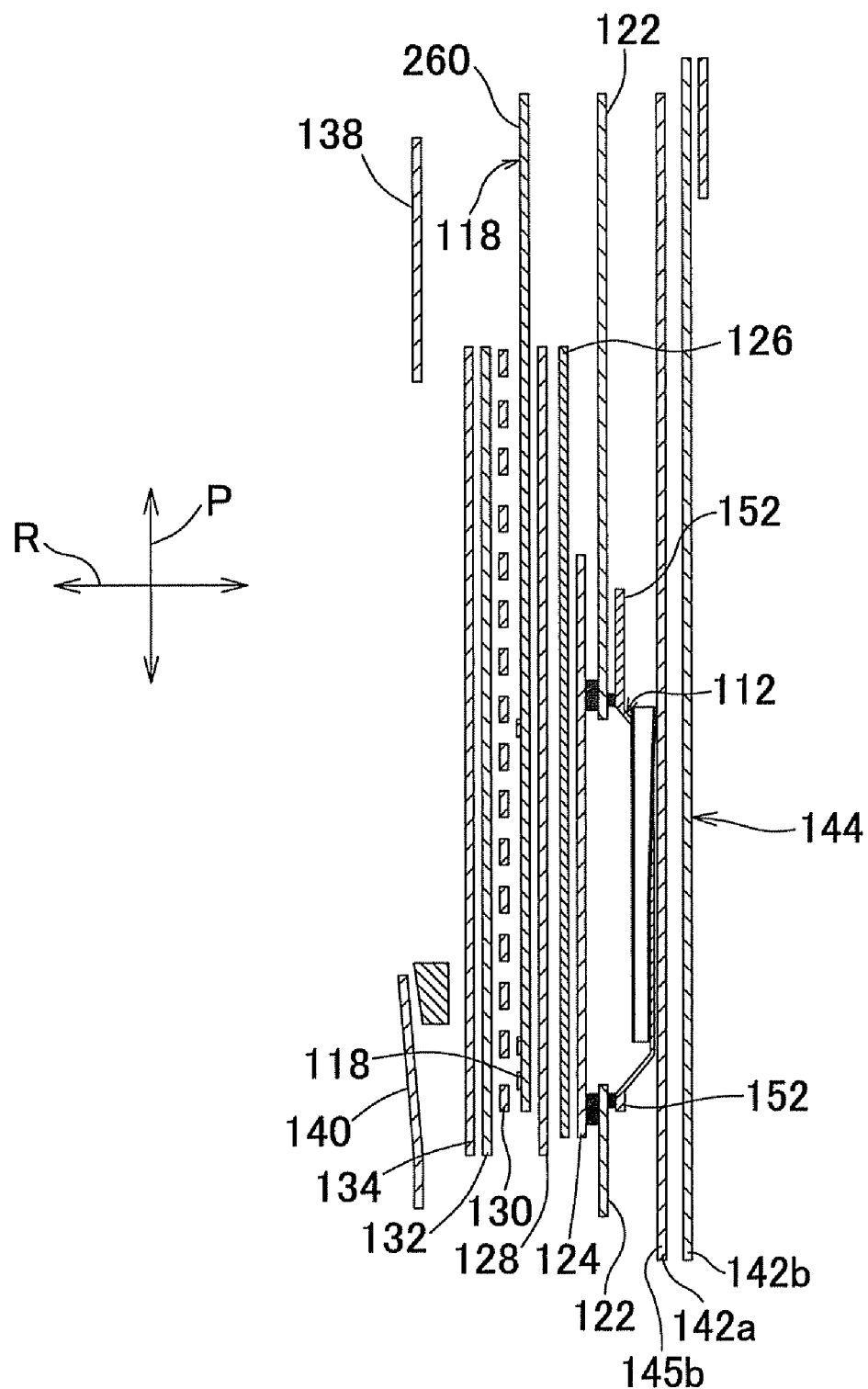
FIG. 5 is a sectional view taken along the line V-V in FIG. 3.

FIG. 3 is a plan view showing the inner side of the urine receiver 102, FIG. 4 is a sectional view taken along the line IV-IV in FIG. 3 and FIG. 5 is a sectional view taken along the line V-V in FIG. 3. In FIGS. 4 and 5, most of the members stacked together in a thickness direction R (see FIG. 4) of the urine receiver 102 are illustrated to be spaced one from another.

Referring to FIGS. 3 and 4, the urine receiver 102 has a length direction P corresponding to the vertical direction of the wearer's body and a width direction Q which is orthogonal to the length direction P. The urine receiver 102 has a width which is relative large in the vicinity of its opposite end sections as viewed in the length direction P and gradually reduced in its middle section. The urine receiver 102 has a thickness direction R also, and comprises the container member 112, a liquid-impervious backsheet 122, a substantially non-breathable liquid-pervious sheet 124, a diffusive sheet 126, a cushion sheet 128, the urine sensor 118, a protective spacer 130 for the urine sensor 118, a protective sheet-like filter 132 for the urine sensor 118, a liquid-pervious skin-contacting sheet 134 and leak-proof barriers 136 stacked in this order from below.

As seen with the urine receiver 102 flattened, both upper and lower ends of the respective leak-proof barriers 136 are covered with first and second end sheets 138, 140 (see FIG. 3).

If the skin-contacting sheet 134 is contaminated with feces discharged from the wearer of the urine receiver 102, it will be no more possible for the urine receiver 102 to absorb urine. In order to deal with this problem, the urine receiver 102 of FIGS. 3 and 4 is provided with a feces sensor 144. Referring to FIG. 4, the feces sensor 144 comprises a pair of electrodes 143a, 143b formed on thermoplastic synthetic resin films 142c, 142d, for example, by an aluminum evaporation technique. The films 142c, 142d are covered with a pair of cover sheets 142a, 142b. The cover sheets 142a, 142b are liquid-pervious so that an aqueous content of feces is permeable therethrough toward the electrodes 143a, 143b. In such a feces sensor 144, the electrodes 143a, 143b extend in the length direction P in parallel to the electrodes 218a, 218b for urine detection. If a lower end section 145b of the feces sensor 144 as viewed in FIGS. 3 and 5 is contaminated with feces, an aqueous content of feces permeates the cover sheet 142a and electrically connects the electrodes 143a, 143b to each other. Thereupon a power source 116a (see FIG. 1) provided in the wiring supplies an alarm unit with current in the form of signal asking for a treatment of feces and an exchange of the urine receiver 102.

Figure 6:
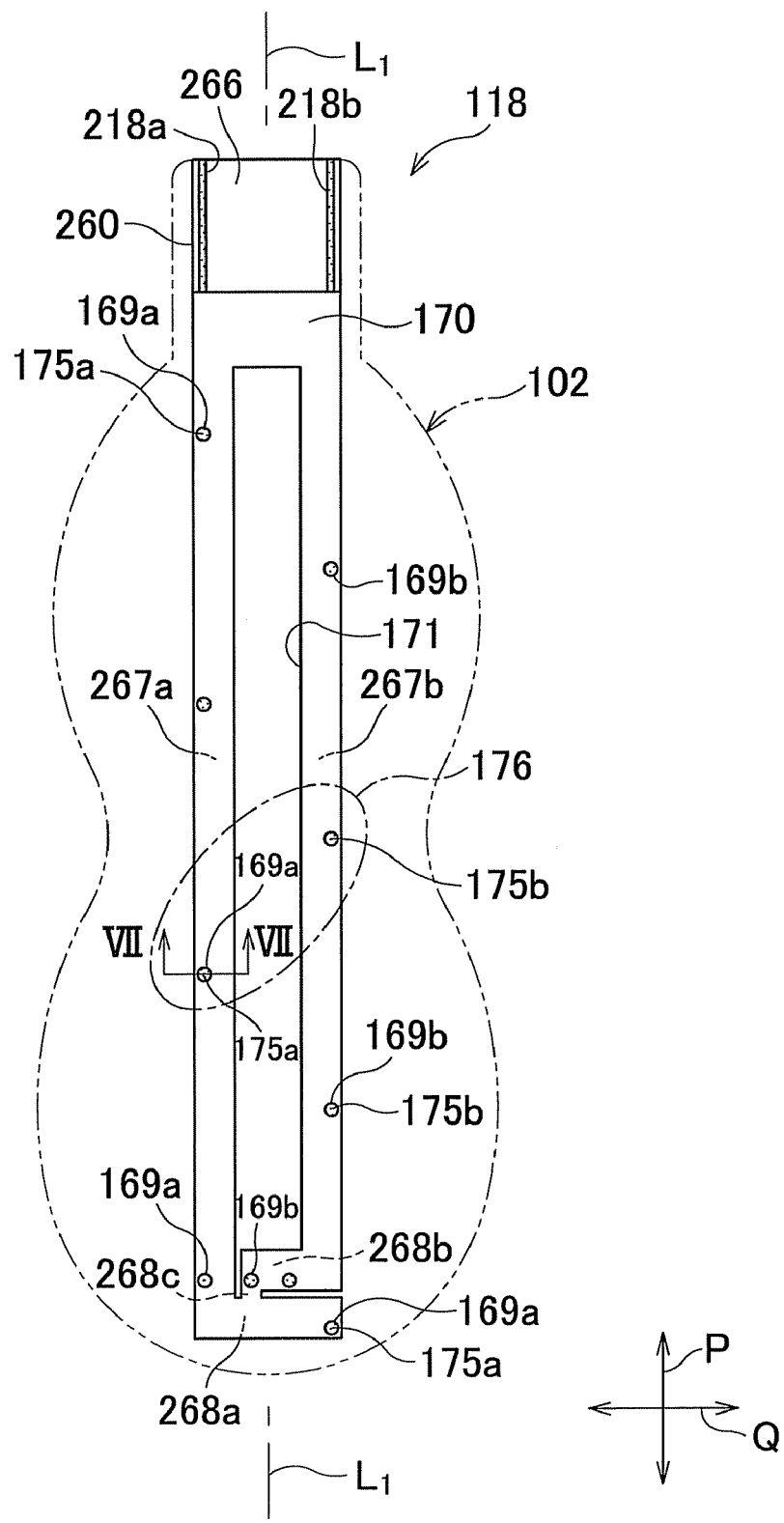
FIG. 6 is a plan view of a urine sensor.

FIG. 6 is a plan view showing the urine sensor 118 used in the urine receiver 102 shown by FIGS. 3 and 4, the contour of the urine receiver 102 being indicated by an imaginary line. The urine sensor 118 comprises film 260 made of thermoplastic synthetic resin such as polyester resin, a pair of the urine detection electrodes 218a, 218b formed on one side of the film 260 and an insulator coating 170 covering most part of these electrodes 218a, 218b. The film 260 has a rectangular shape which is relatively long in the length direction P and a middle region thereof as viewed in the width direction Q is cut away to form a substantially rectangular opening 171. Such a film 260 in FIG. 6 is contoured by an upper end 266 to be held by the clip 120, side portions 267a, 267b lying below the upper end 266 and along the opening 171 so as to extend on both sides a center line $L_1$-$L_1$ bisecting the width of the urine sensor 118, and lower ends 268a, 268b lying further below so as to be contiguous to the side portions 267a, 267b, respectively. The lower ends 268a, 268b are, in turn, contiguous to each other by the intermediary of a joint portion 268c. Most part of the surface of the film 260 carrying the electrodes 218a, 218b is covered with the insulator coating 170 except the upper end 266 at which the electrodes 218a, 218b are exposed. A plurality of small regions found on the side portions 267a, 267b as well as the lower ends 268a, 268b respectively correspond to coating-free zones 169a, 169b in which no insulator coating 170 is formed and the urine detecting parts 175a or 175b of the electrode 218a or 218b, respectively, are exposed.

Figure 7:
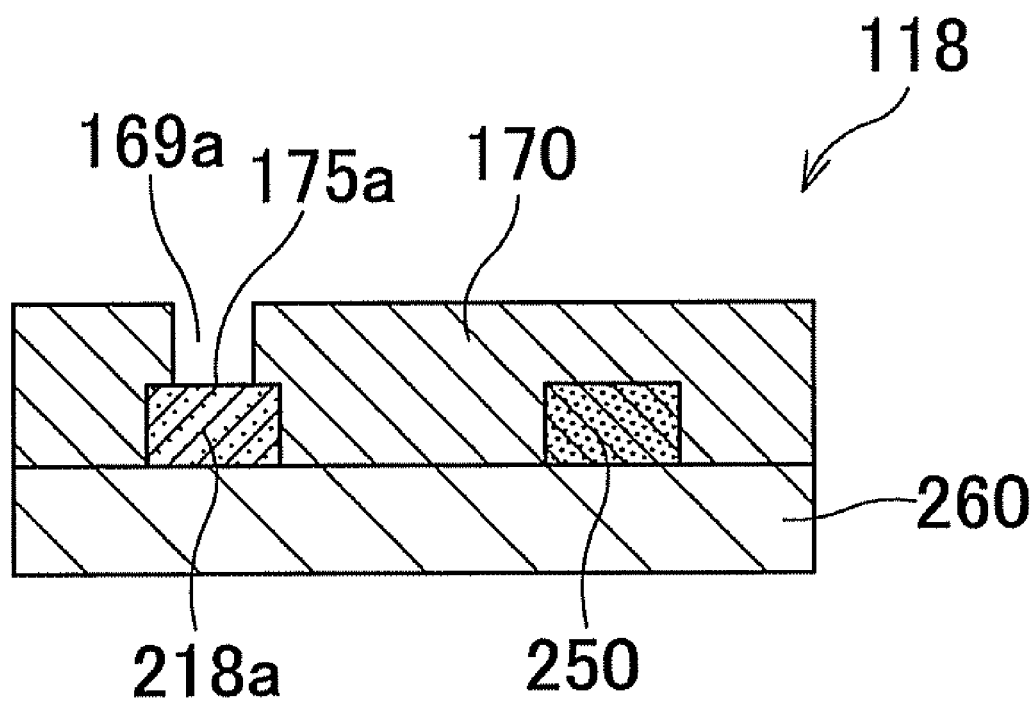
FIG. 7 is a sectional view taken along the line VII-VII in FIG. 6.

FIG. 7 is a sectional view taken along the line VII-VII in FIG. 6. As shown, the film 260 has on its upper surface, in addition to the urine detection electrode 218a, a wiring breakage detection circuit 250 and the urine detecting part 175a of the electrode 218a is exposed in the coating-free region 169a. It should be understood that the circuit 250 is entirely covered with the insulator coating 170.

Figure 8:
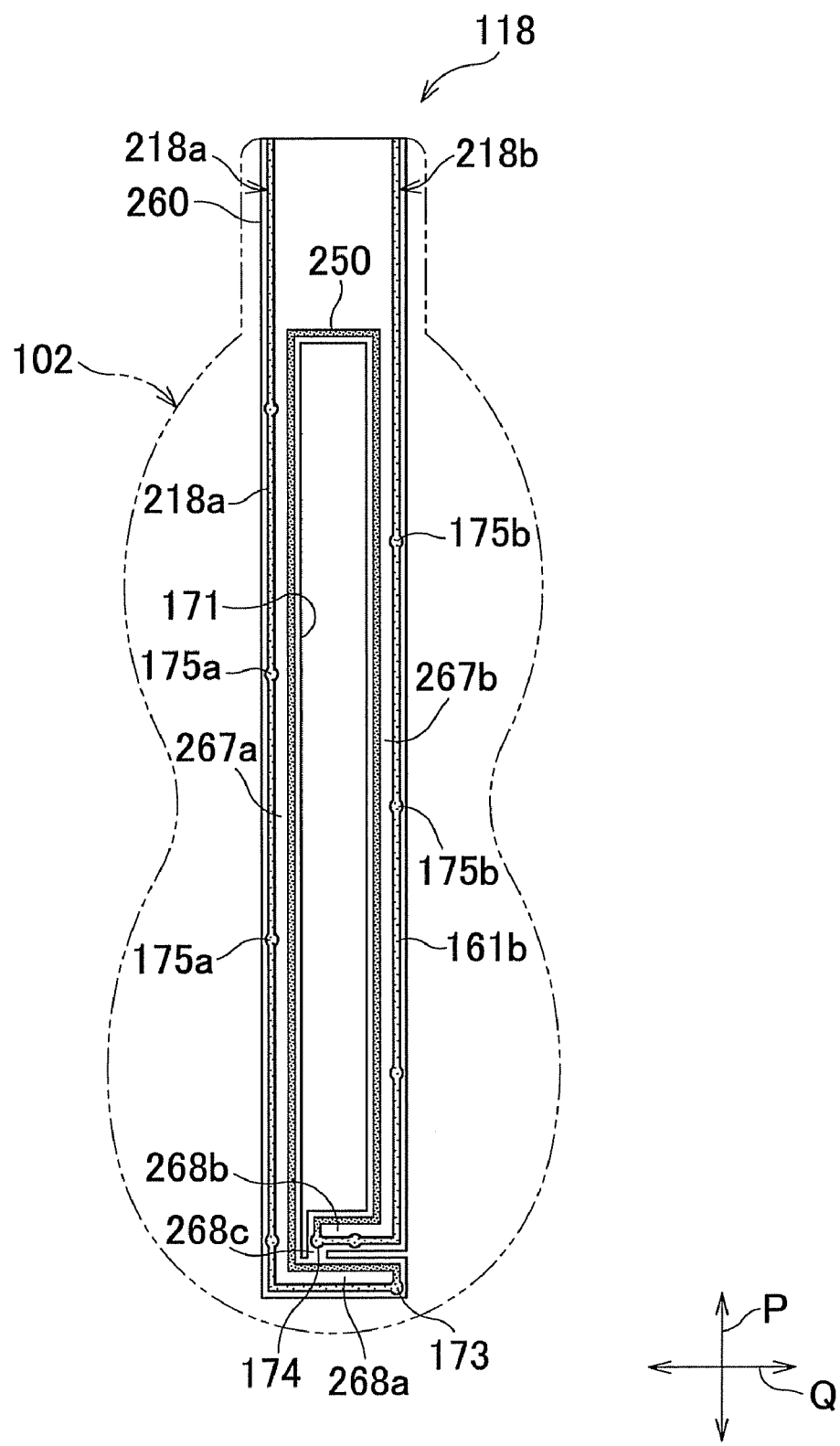
FIG. 8 is a plan view of the urine sensor not covered with insulator coating.

FIG. 8 is a plan view showing the urine sensor 118 in the stage before covered with the insulator coating 170. On one side of the side portion 267a and the lower end 268a of the film 260 there is urine detection electrode 218a which is substantially L-shaped and on one side of the side portion 267b and the lower end 268b of the film 260 there is the urine detection electrode 218b which is substantially inverted L-shaped. The circular regions 175a, 175b of these electrodes 218a, 218b are exposed in the coating-free zones 169a, 169b as shown by FIG. 6. The wiring breakage detection circuit 250 is defined between the electrodes 218a, 218b. The circuit 250 is electrically connected to the respective lower ends 173, 174 of the urine detection electrodes 218a, 218b and extends along the peripheral edge of the opening 171 as shown.

A preferable example of the film 260 in such a urine sensor 118 is polyester film having a thickness in a range of 50 to 100 μm. The electrodes 218a, 218b may be prepared by printing conductive ink or conductive coating material in desired shapes on the film 260. The conductive ink or the conductive coating material may contain, as conductive materials, carbon black of 3 to 7% by weight, artificial graphite such as carbon graphite of 10 to 30% by weight and an appropriate amount of silver powder. Each of the preferred electrodes 218a, 218b has a width in a range of 0.5 to 2 mm, of which a value of resistance is 150 KΩ or less and a diameter of the coating-free region 169a or 169b is in a range of 1 to 2 mm. The wiring breakage detection circuit 250 may be prepared, for example, by printing conductive ink containing carbon black of 3 to 7% by weight and artificial graphite of 5 to 10% by weight on the film 260 in a desired shape. This circuit 250 has a value of resistance substantially higher than those of the urine detection electrodes 218a, 218b and preferably has a width in a range of 0.3 to 1 mm and a value of resistance in a range of 2 to 10 MΩ.

When the urine sensor 118 of FIG. 6 is used in the urine receiver 102, weak current A normally flows from the power supply 116a included in the electrical wiring 116 to the electrodes 218a, 218b and the circuit 250 electrically connected with these electrodes 218a, 218b via the clip 120. In response to such weak current A, a circuit 110 including the wiring 116 decides that the urine detection electrodes 218a, 218b are normally functioning. If the current A is not detected, on the contrary, the circuit 110 decides that any failure, for example, wiring breakage has occurred in the urine detection electrodes 218a, 218b and thereupon causes the pump unit 108 to output a signal requesting a prompt exchange of the urine sensor 118. Referring to FIG. 6, urine discharged in a range circled by an imaginary line 176 moves into the coating-free zones 169a, 169b provided on the side portions 267a, 267b, respectively, in contact with the urine detection electrodes 175a, 175b and thereupon the electrode 218a on the side portion 267a and the electrode 218b on the side portion 267b are electrically connected to each other via urine. Consequently, the value of resistance between the electrodes 218a, 218b becomes lower than the value of resistance across the circuit 250, and the electric current flows not across the wiring breakage detection circuit 250 having the higher value of resistance but across urine. When electric current B flowing across urine becomes remarkably higher than the electric current A flowing across the circuit 250, the circuit 110 detects a sudden change in the value of the electric current or the correspondingly sudden change in the value of voltage or resistance and immediately detects urination. Based on the signal generated in response to such a change, the pump unit 108 activates the pump to suck urine and then shuts down the pump as the value of resistance between the electrodes 218a, 218b sufficiently increases.

In the urine sensor 118 of FIG. 6, the coating-free zones 169a, 169b for exposing the urine detecting elements 175a, 175b of the urine sensor 118 are formed on the side portions 267a, 267b in asymmetry about the center line $L_1$-$L_1$ as illustrated to achieve an advantageous effect as follows. Assumed that the urine receiver 102 is folded in two in the length direction P during use thereof and consequently the skin-contacting sheet 134 wet with urine is formed with a straight crease extending across the receiver 102 so as to pass through the coating-free zones 169a, 169b, the skin-contacting sheet 134 wet with urine will come in contact with the electrodes 218a, 218b and the pump unit 108 which has completed suction of urine will be erroneously activated again. Such erroneous activation can be easily avoided by the coating-free zones 169a, 169b arranged in asymmetric relation as shown. In addition to these coating-free zones 169a, 169b, the film 260 has on the lower ends 268a, 268b and in the vicinity thereof a plurality of additional coating-free zones 169a, 169b arranged adjacent one to another. Owing to these additional coating-free zones 169a, 169b the urine receiver 102 can suck quickly an amount of urine which may rapidly flow downward immediately after urination as viewed in FIG. 6, instead of flowing toward the liquid-pervious sheet 124. The layout of the coating-free zones 169a, 169b is not limited to one as illustrated and it is possible to distribute these zones 169a, 169b in a different manner on the side portions 267a, 267b in a manner different from that of FIG. 6.

Figure 9:
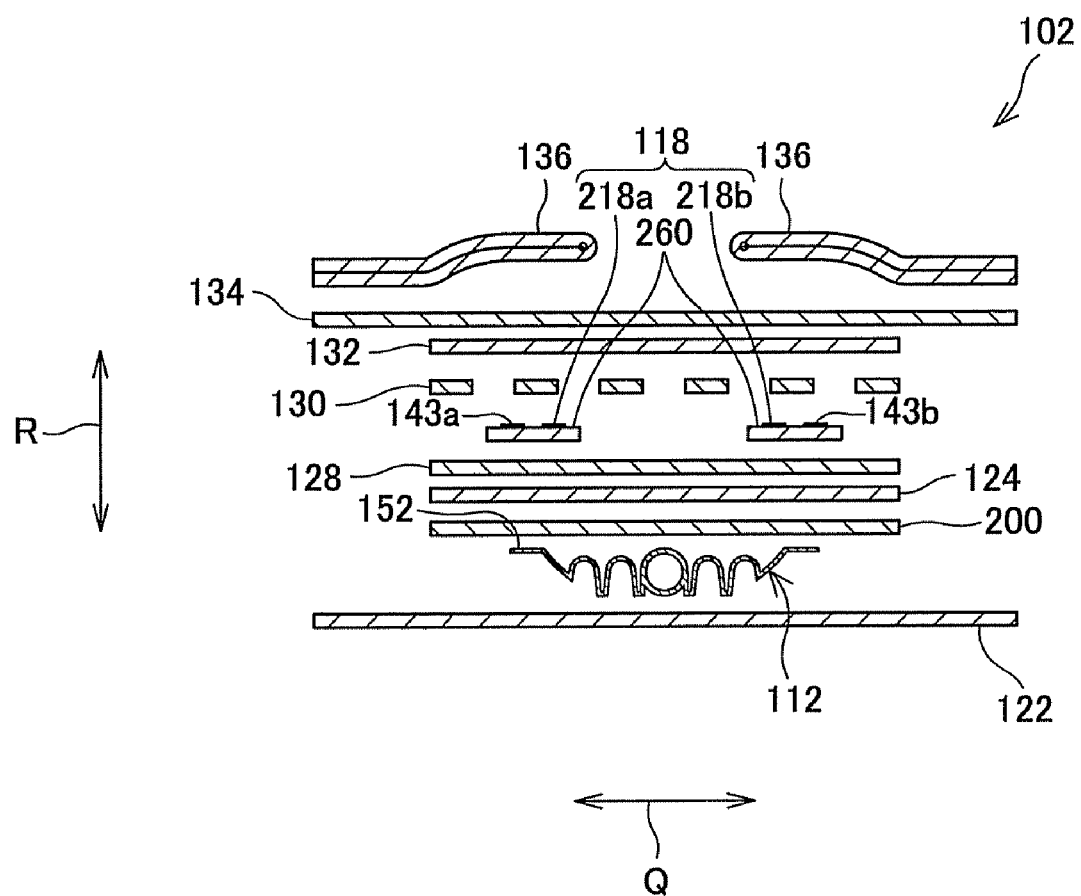
FIG. 9 is a view similar to FIG. 4, showing one embodiment of the urine receiver.
Figure 10:
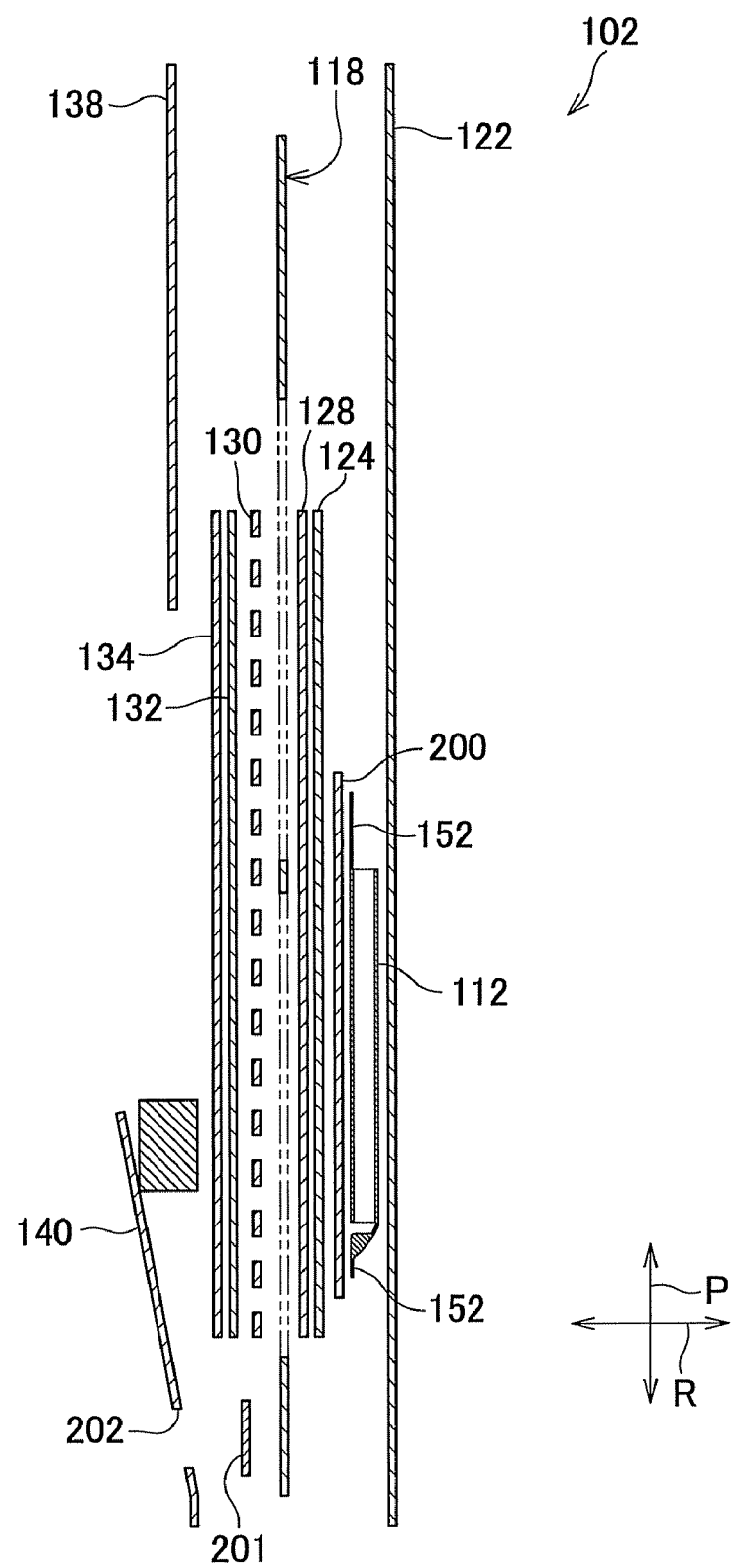
FIG. 10 is a view similar to FIG. 5, showing another embodiment of the urine receiver.

FIGS. 9 and 10 are views similar to FIGS. 4 and 5, respectively, showing one embodiment of the urine receiver 102 in which the respective members stacked one upon another in the thickness direction R are spaced one from another. This urine receiver 102 is provided on the outer side (i.e., lower side as viewed in FIGS. 9 and 10) of the container member 112 with the liquid-impervious backsheet 122 extending outward from the peripheral edge of the container member 112 in the length direction P as well as in the width direction Q. The container member 112 is provided on its inner side with a bond sheet 200, the substantially air-impermeable liquid-pervious sheet 124, the cushion sheet 128, the urine sensor 118, the spacer 130, the filter 132, the skin-contacting sheet 134 and the leak-proof barriers 136 placed one upon another as illustrated.

The bond sheet 200 is used to facilitate the liquid-pervious sheet 124 to be attached to the flange 152 of the container member 112. For example, if the container member 112 is made of polyethylene and the liquid-pervious sheet 124 is made of material having a melting temperature higher than that of polyethylene such as rayon fiber, polypropylene fiber or polyester fiber, the bond sheet 200 is prepared from a resinous material having a melting temperature substantially same as or lower than that of the container member 112. For example, the bond sheet 250 is a spun-bonded nonwoven fabric of polyethylene/polypropylene composite fiber of side-by-side type. The liquid-pervious sheet 124 can be easily attached to the flange 152 over the entire circumference thereof by melting polyethylene contained in the composite fiber interposed between the liquid-pervious sheet 124 and the flange 152 under compression in the thickness direction R. Such a bond sheet 200 may be used so as to cover the flange 152 and the upper opening entirely or so as to cover the flange 152 alone.

The liquid-pervious sheet 124 of FIGS. 9 and 10 has the both functions of the liquid-pervious sheet 124 of FIGS. 4 and 5 and the diffusive sheet 126 of FIGS. 4 and 5. This liquid-pervious sheet 124 is formed, for example, by spun lace nonwoven fabric containing rayon fiber at a rate of 40% by weight or more with a fineness in a range of 1 to 6 dtex and a length in a range of 20 to 60 mm. The liquid-pervious sheet 124 may also contain thermoplastic synthetic fiber at a rate of 60% by weight or less with a fineness in a range of 1 to 6 dtex and a length in a range of 20 to 60 mm. Similarly to the liquid-pervious sheet 124 of FIG. 4, the liquid-pervious sheet 124 of FIGS. 9 and 10 has air-permeability in a range of 0 to 100 $cc/cm^2/sec$ in the wet condition and a range of 20 to 200 $cc/cm^2/sec$ in the dried condition. The liquid-pervious sheet 124 containing rayon fiber at a rate of 40% by weight or more can diffuse urine as quickly as the diffusive sheet 126 of FIG. 4. While the specified air-permeability is preferably met by the liquid-pervious sheet 124 itself, the specified air-permeability may be also met by the liquid-pervious sheet 124 placed upon and at least partially bonded to the bond sheet 200 which is entirely covering the opening of the container member 112 as shown by FIGS. 9 and 10.

The cushion sheet 128 may be formed by the same material as that of the cushion sheet 128 of FIGS. 4 and 5 and may have the same size as the liquid-pervious sheet 124.

The urine sensor 118 includes the urine detection electrodes 218a, 218b (see FIG. 9) formed by coating the inner surface of the film 260 with conductive material. The film 260 extends in the length direction P substantially to the both ends of the backsheet 122. This film 260 is distinguished from the film 260 of FIG. 5 in that this film 260 is formed on the same surface with the paired feces detection electrodes 143a, 143b (see FIG. 9) also.

The spacer 130 may be formed by the same material as that of the spacer 130 of FIGS. 4 and 5 and may have the same size as the liquid-pervious sheet 124. The spacer 130 extends in the length direction P but does not extend downward as far as the spacer 130 might cover the feces detecting elements 144d, 144e (see FIG. 11) in the feces detection electrodes 143a, 143b.

The filter 132 and the skin-contacting sheet 134 may be formed by the same materials as those for the filter 132 and the skin-contacting sheet 134 of FIGS. 4 and 5, respectively. The filter 132 has the same size as the liquid-pervious sheet 124. The skin-contacting sheet 134 has the same dimension as that of the liquid-pervious sheet 124 in the length direction P but has a dimension which is larger than the liquid-pervious sheet 124 and substantially same as the backsheet 112 in the width direction Q.

The ends of the urine receiver 102 opposed to each other in the length direction P are respectively provided with the end sheets 138, 140 (see FIG. 10). These end sheets 138, 140 respectively cover the ends (not shown) of the leak-proof barrier 136 which is opposed to each other in the length direction P in the same manner as in FIG. 3.

Referring to FIGS. 8 and 9, the liquid-pervious sheet 124, the cushion sheet 128, the urine sensor 118, the spacer 130, the filter 132 and the skin-contacting sheet 134 stacked one on another are bonded one to another in the same manner as in FIGS. 4 and 5. However, a portion of the backsheet 122 extending outward beyond the flange 152 of the container member 112 is bonded to the skin-contacting sheet 134 and the other sheets and preferably further to the outer surface of the bottom of the container member 112. The leak-proof barriers 136 are bonded to the skin-contacting sheet 134 and a portion of the backsheet 122 extending outward beyond the peripheral edge of the skin-contacting sheet 134.

Referring to FIG. 10, the feces detecting element 144d, 144e of the feces detection electrodes 143a, 143b are covered with nonwoven fabric cover sheet 201 (see FIG. 10) allowing the moisture content in feces to permeate therethrough. The end sheet 140 lying above the cover sheet 201 is formed with a through-hole 202 so that the end sheet 140 might cover the detecting elements 144d, 144e. The through-hole 202 is to be located in the vicinity of the anus of the wearer of the urine receiver 102.

FIG. 11 is a plan view showing the urine sensor 118 used in the urine receiver 102 of FIGS. 9 and 10 as partially in sectional view. The urine sensor 118 comprises a pair of urine detection electrodes 218a, 218b formed on the inner surface of the liquid-impervious thermoplastic synthetic resin film 260, a pair of feces detection electrodes 143a, 143b and a wiring breakage detection circuit 250. Most part of the electrodes 218a, 218b, 143a, 143b and the entire wiring breakage detection circuit 250 are covered with the insulator coating 170 partially shown in a sectional view. The film 260 is formed in the middle region as viewed in the width direction Q with two openings 171, 172 aligned with each other in the length direction P. A bridge 183 serving to prevent deformation of the film 260 is defined between these openings 171, 172. The pair of electrodes 218a, 218b as well as the pair of electrodes 143a, 143b are formed so as to be opposed to each other about the openings 171, 172, respectively, and the wiring breakage detection circuit 250 extends along the respective edges of the openings 171, 172 so as to connect the opposite ends of the pair of urine detection electrodes 218a, 218b. Referring to FIG. 11, the urine detection electrodes 218a, 218b respectively have the urine detecting elements 175a, 175b exposed in portions 169a free from the insulator coating 170 while the feces detection electrodes 143a, 143b respectively have feces detecting elements 144d, 144e in the vicinity of the respective lower ends of the urine detection electrodes 218a, 218b and not covered with the coating 170. These urine detecting elements 175a, 175b and the feces detecting elements 144d, 144e are substantially symmetric about the center line $L_1$-$L_1$. The urine detection electrodes 218a, 218b are formed on the upper ends thereof with connectors 218c, 218d while the feces detection electrodes 143a, 143b are formed on the upper ends with connectors 244a, 244b. These connectors 218c, 218d and 244a, 244b are held by the clip 120 of FIG. 2. When the urine detecting elements 175a, 175b are electrically connected to each other via urine between the paired urine detection electrodes 218a, 218b, electric current flows between the urine detection electrodes 218a, 218b as in the case of the urine sensor of FIG. 6 and thereupon the pump unit 108 is activated. When the feces detecting elements 144d, 144e are electrically connected to each other via aqueous content in feces between the paired feces detection electrodes 143a, 143b, electric current flows between the feces detection electrodes 143a, 143b and thereupon the pump unit 108 is informed of defecation as in the case of the urine receiver 102 of FIGS. 4 and 5.

It should be noted that weak current normally flows in the wiring breakage detection circuit 250 as in the case of the urine sensor 118 of FIG. 8 so that a wiring breakage alarm device (not shown) included in the pump unit 108 is activated due to a change of electric current based on a damage of the urine detection electrodes 218a and/or 218b and urges to set off exchange of the urine receiver 102.

The present invention presents a urine receiver which can efficiently and quickly suck urine.

The entire discloses of Japanese Patent application Nos. 2005-204978 and 2006-187166 filed on Jul. 13, 2005 and Jul. 6, 2006, respectively, including specification, drawings and abstract are herein incorporated by reference in their entirety.

What is claimed is:

1. A urine sensor to be used in a urine receiver comprising a urine collecting member to be put on a wearer's body with the inner side placed against a urethral and a skin thereabout and a urine detecting member to be interposed between said skin and said urine collecting member and serving to detect urine discharged from said urethral, wherein said urine receiver is connected to a vacuum suction means provided separately of said urine receiver so that said vacuum suction means may be activated in response to a detection signal output from said urine detecting member to suck said urine into said urine collecting member, wherein said urine sensor comprises
thermoplastic synthetic resin film having a length direction, a width direction and a thickness direction being orthogonal one to another,
a pair of electrodes formed on a surface of said film, each of said electrodes having opposite top and bottom surfaces, wherein the bottom surface is covered by said film, and
an electrically insulating coating formed on said surface to cover the top surface of each of said electrodes,
said film being formed along a center line with an opening, which is elongated in the length direction, and both side portions of said film along said opening being respectively provided with said electrodes extending in said length direction,
each of said electrodes being provided at one of opposite ends thereof as viewed in said length direction with an electrical connector to be connected to said vacuum suction means,
and said insulating coating being formed between said opposite ends of said electrodes with a plurality of through-holes in which said electrodes may come in contact with said urine flowing into said through-holes, wherein said through-holes extend in the thickness direction through the insulating coating, without extending through the electrodes, and partially exposing the top surfaces of the electrodes.

2. The urine sensor defined by claim 1, wherein the respective opposite ends of said electrodes are electrically connected to each other via a circuit having an electric resistance higher than those of said electrodes.

3. The urine sensor defined by claim 2, wherein each of said electrodes has an electric resistance of 150 KΩ or less and said circuit has an electric resistance of in a range of 2 to 10 MΩ.

4. The urine sensor defined by claim 2, wherein the circuit connected to the opposite ends of the electrodes is entirely covered by the insulating coating.

5. The urine sensor defined by claim 2, wherein said ends of the electrodes are free of direct contact with each other, and said opposite ends of the electrodes are connected with each other via said circuit which extends along a peripheral edge of the opening.

6. The urine sensor defined by claim 1, wherein said urine sensor further includes a pair of feces detection electrodes extending in parallel to said electrodes; and
said feces detection electrodes are also covered with said electrically insulating coating and have coating-free zones in the vicinity of said ends opposed to said respective one ends so that said coating-free zones are allowed to contact feces to be detected.

7. The urine sensor defined by claim 6, wherein said electrodes, a circuit extending between said opposite ends of the electrodes and said feces detection electrodes are formed by conductive ink or conductive coating material.

8. The urine sensor defined by claim 1, wherein said film is liquid-impervious.

9. The urine sensor defined by claim 8, wherein said through-holes extend in the thickness direction through the insulating coating only, without extending through the electrodes or the film.

10. The urine sensor defined by claim 1, wherein said ends of the electrodes are not covered by and are free of direct contact with the insulating coating.

11. The urine sensor defined by claim 1, wherein said electrodes comprise a first substantially L-shaped electrode and a second substantially inverted L-shaped electrode opposite to the first electrode in the length direction.

12. The urine sensor defined by claim 11, wherein a length of said first electrode is different from that of said second electrode.

13. A urine sensor to be used in a urine receiver, said urine receiver comprising: a urine collecting member, said urine sensor adapted to be interposed between a wearer and the urine collecting member for detecting urine, a vacuum suction element electrically connectable to the urine sensor and adapted to be activated in response to a detection signal output from the urine sensor to suck urine into the urine collecting member, the urine sensor having a length direction and a width direction orthogonal to the length direction, said urine sensor comprising:
a film having, in the width direction, an opening elongated in the length direction, and first and second side portions on opposite sides of said opening;
first and second electrodes extending on said first and second side portions of said film in the length direction, and being covered from below by the side portions, respectively; and
an electrically insulating coating covering said electrodes from above, and a plurality of through-holes formed through the electrically insulating coating for allowing the urine to flow into the through-holes to directly contact said electrodes;

wherein said film is liquid-impervious.

14. The urine sensor defined by claim 13, wherein each of the electrodes comprises a first end and a second end opposite to the first end.

15. The urine sensor defined by claim 13, wherein said first electrode is formed of a substantially L-shape, and said second electrode is formed of an substantially inverted L-shape opposite to the L-shape of the first electrode in the length direction, and said first electrode has a length different from that of said second electrode.

16. The urine sensor defined by claim 13, wherein said first and second electrodes have a plurality of portions having enlarged widths where said through-holes are positioned.

17. A urine sensor to be used in a urine receiver, said urine receiver comprising: a urine collecting member, said urine sensor adapted to be interposed between a wearer and the urine collecting member for detecting urine, a vacuum suction element electrically connectable to the urine sensor and adapted to be activated in response to a detection signal output from the urine sensor to suck urine into the urine collecting member, the urine sensor having a length direction and a width direction orthogonal to the length direction, said urine sensor comprising:

a film having, in the width direction, an opening elongated in the length direction, and first and second side portions on opposite sides of said opening;

first and second electrodes extending on said first and second side portions of said film in the length direction, and being covered from below by the side portions, respectively, wherein each of the electrodes comprises a first end and a second end opposite to the first end;

an electrically insulating coating covering said electrodes from above, and a plurality of through-holes formed through the electrically insulating coating for allowing the urine to flow into the through-holes to directly contact said electrodes; and a circuit connecting to and between the second ends of the electrodes, respectively, wherein said circuit is entirely covered by the insulating coating and has an electric resistance higher than those of said electrodes.

18. The urine sensor defined by claim 17, wherein said first ends of the electrodes are not covered by and are free of direct contact with the insulating coating.

19. The urine sensor defined by claim 18, wherein each of said electrodes includes an electrical connector formed on the respective first end of the electrode, said electrical connector adapted to be connected to the vacuum suction element.

20. The urine sensor defined by claim 17, wherein said first ends of the electrodes are free of direct contact with each other, and said second ends of the electrodes are connected with each other via said circuit which extends along a peripheral edge of the opening.

* * * * *